US00PP29510P2

(12) United States Plant Patent
Winslow

(10) Patent No.: US PP29,510 P2
(45) Date of Patent: Jul. 17, 2018

(54) ***IPOMOEA* PLANT NAMED 'BALSOTOWIME'**

(50) Latin Name: *Ipomoea batatas*
Varietal Denomination: Balsotowime

(71) Applicant: Ball Horticultural Company, West Chicago, IL (US)

(72) Inventor: Benjamin K. Winslow, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/530,802

(22) Filed: Mar. 1, 2017

(51) Int. Cl.
*A01H 5/12* (2018.01)

(52) U.S. Cl.
USPC ..... Plt./258

(58) Field of Classification Search
USPC ..... Plt./258, 263.1
See application file for complete search history.

*Primary Examiner* — Susan Beth McCormick Ewoldt
(74) *Attorney, Agent, or Firm* — Audrey Charles

(57) ABSTRACT

A new and distinct cultivar of an ornamental *Ipomoea* plant named 'Balsotowime', characterized by its lime-green colored foliage, and vigorous, climbing growth habit, is disclosed.

1 Drawing Sheet

Latin name of genus and species of plant claimed: *Ipomoea batatas*.

Variety denomination: 'Balsotowime'.

BACKGROUND OF THE INVENTION

The present invention relates to a new and distinct cultivar of *Ipomoea* plant botanically known as *Ipomoea batatas* and hereinafter referred to by the cultivar name 'Balsotowime'.

The new cultivar originated in a controlled breeding program in Arroyo Grande, Calif. during January 2015. The objective of the breeding program was the development of ornamental *Ipomoea* cultivars with a vigorous, climbing habit.

The new ornamental *Ipomoea* cultivar is the result of cross-pollination. The female (seed) parent of the new cultivar is the proprietary *Ipomoea batatas* breeding selection coded 188-054, not patented, characterized by its light bronze-colored foliage and vigorous, spreading growth habit. The male (pollen) parent of the new cultivar is the proprietary *Ipomoea batatas* breeding selection coded 098-001, not patented, characterized by its light lime-green colored foliage and moderately vigorous, spreading growth habit. The new cultivar was discovered and selected as a single plant within the progeny of the above stated cross-pollination during May 2015 in a controlled environment in Arroyo Grande, Calif.

Asexual reproduction of the new cultivar by terminal stem cuttings since May 2015 in Arroyo Grande, Calif., and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balsotowime' as a new and distinct cultivar of *Ipomoea* plant:

1. Lime-green colored foliage; and
2. Vigorous, climbing growth habit.

Plants of the new cultivar differ from plants of the female parent primarily in having a different foliage color. Plants of the new cultivar differ from plants of the male parent primarily in having increased growth vigor.

Of the many commercially available ornamental *Ipomoea* cultivars, the most similar in comparison to the new cultivar is SolarPower Lime 'Balsolalime', U.S. Plant Pat. No. 26,552. However, in comparison, plants of the new cultivar differ from plants of 'Balsolalime' in at least the following characteristics:

1. Plants of the new cultivar have a different growth habit than plants of 'Balsolalime'; and
2. Plants of the new cultivar have a leaf shape that is different from plants of 'Balsolalime'.

BRIEF DESCRIPTION OF THE PHOTOGRAPHS

The accompanying photographs show, as nearly true as it is reasonably possible to make the same in color illustrations of this type, typical foliage characteristics of the new cultivar. Colors in the photographs differ slightly from the color values cited in the detailed description, which accurately describes the colors of 'Balsotowime'. The plants were grown in 4.5-inch pots for 9 weeks in a greenhouse in West Chicago, Ill. Plants were pinched one week after transplant.

DETAILED BOTANICAL DESCRIPTION

Figure 1:
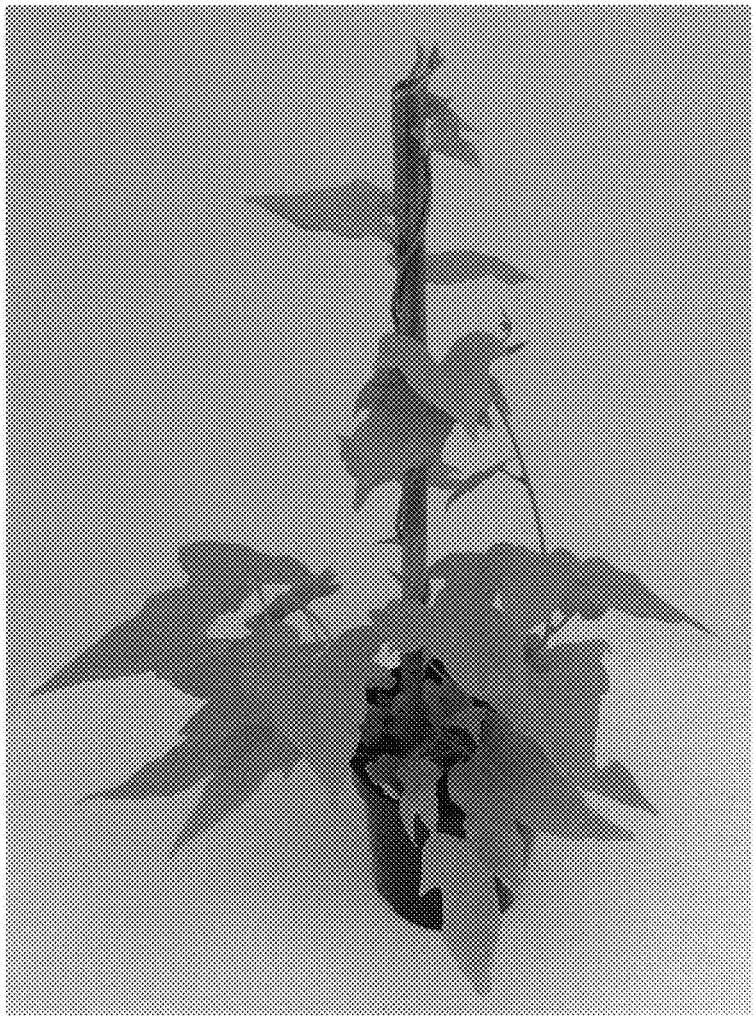
FIG. 1 illustrates a side view of the overall growth and habit of 'Balsotowime'.
Figure 2:
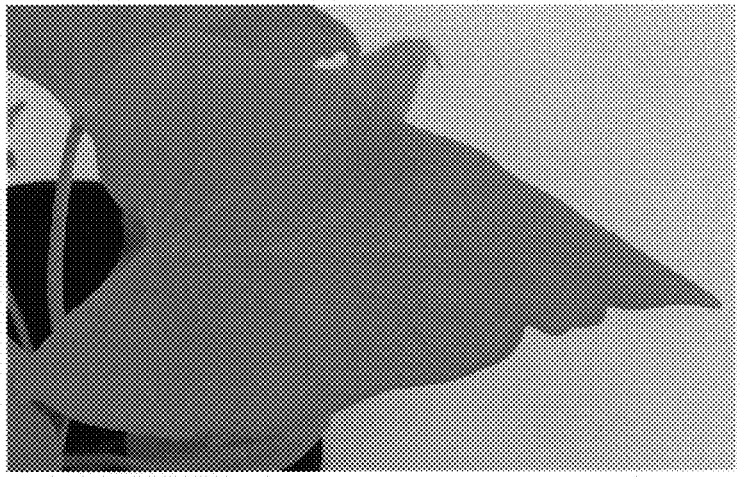
FIG. 2 illustrates a close-up view of an individual leaf of 'Balsotowime'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in February 2017 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4.5-inch pots for 9 weeks in a greenhouse utilizing a soilless growth medium. Plants were pinched one week after transplant. Greenhouse temperatures were maintained at approximately 66° F. to 70° F. (19° C. to 21° C.) during the day and approximately 58° F. to 62° F. (14° C. to 17° C.) during the night. Greenhouse light levels of 2,500 footcandles to 6,000 footcandles were maintained during the day. Measurements and numerical values represent averages of typical plants.

Botanical classification: *Ipomoea batatas* cultivar Balsotowime.

Parentage:

*Female parent*.—Proprietary *Ipomoea batatas* breeding selection coded 188-054, not patented.

*Male parent*.—Proprietary *Ipomoea batatas* breeding selection coded 098-001, not patented.

Propagation:

*Type cutting*.—Terminal stem.

*Time to initiate roots*.—Approximately 3 to 4 days.

*Time to produce a rooted cutting*.—Approximately 21 to 28 days.

*Root description*.—Fibrous, medium thickness.

*Rooting habit*.—Freely branching.

*Tuber description*.—Not available, tuber formation not observed.

Plant description:

*Commercial crop time*.—Approximately 4 to 5 weeks from a rooted cutting to finish in a 10 cm pot.

*Growth habit and general appearance*.—Vigorous, climbing growth habit.

*Size*.—Height (as supported for climbing): Approximately 32.0 cm. Height (unsupported for climbing): Approximately 13.0 cm. Length (unsupported for climbing): Approximately 42.0 cm. Width: Approximately 29.0 cm.

*Branching habit*.—Freely branching, pinching enhances basal branching. Quantity of main branches per plant: Approximately 2.

*Branch*.—Shape: Round. Strength: Strong, flexible. Length: Approximately 42.0 cm. Diameter: Approximately 3.0 mm. Length of central internode: Approximately 4.0 cm. Texture: Glabrous. Color of young and mature stems: 145B.

Foliage description:

*General description*.—Quantity of leaves per main branch: Approximately 13. Fragrance: None detected. Form: Simple. Arrangement: Alternate, spiral.

*Leaves*.—Shape: Cordate with two shallow lateral lobes. Margin: Entire. Apex: Acuminate. Base: Cordate. Venation pattern: Palmate with arcuate venation in the center lamina. Length of mature leaf: Approximately 10.5 cm. Width of mature leaf: Approximately 7.0 cm. Texture of upper and lower surfaces: Glabrous. Color of upper surface of young foliage: Closest to but more green than 145A with slightly darker venation. Color of lower surface of young foliage: Closest to 147D with venation of 145C. Color of upper surface of mature foliage: Closest to but darker than N144D with venation or 145B. Color of lower surface of mature foliage: Closest to but more green than 147D with venation of 145D.

*Petiole*.—Length: Approximately 4.5 cm. Diameter: Approximately 3.0 mm. Texture: Glabrous. Color: Between 145B and 145C with a faint tint of 187B at leaf attachment.

Flowering description: Not available, flower and seed formation not observed. The new ornamental *Ipomoea* cultivar is grown as a foliage plant and is not grown under conditions that are conducive to flower production.

Disease and pest resistance: Resistance to pathogens and pests common to *Ipomoea* has not been observed.

What is claimed is:

1. A new and distinct cultivar of an ornamental *Ipomoea* plant named 'Balsotowime', substantially as herein illustrated and described.

* * * * *